(12) United States Patent
Yoshino et al.

(10) Patent No.: US 9,174,435 B2
(45) Date of Patent: Nov. 3, 2015

(54) LIQUID EJECTING DEVICE

(75) Inventors: Hiroyuki Yoshino, Suwa (JP); Kunio Tabata, Shiojiri (JP); Atsushi Oshima, Shiojiri (JP); Noritaka Ide, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 507 days.

(21) Appl. No.: 13/570,867

(22) Filed: Aug. 9, 2012

(65) Prior Publication Data
US 2013/0038654 A1    Feb. 14, 2013

(30) Foreign Application Priority Data

Aug. 12, 2011 (JP) ................................. 2011-176576

(51) Int. Cl.
*B41J 2/045* (2006.01)
*B41J 2/175* (2006.01)

(52) U.S. Cl.
CPC .......... *B41J 2/04541* (2013.01); *B41J 2/04581* (2013.01); *B41J 2/175* (2013.01)

(58) Field of Classification Search
CPC .................................................. B41J 2/04541
See application file for complete search history.

(56) References Cited

U.S. PATENT DOCUMENTS

| | | | |
|---|---|---|---|
| 7,244,007 B2 | 7/2007 | Ishizaki | |
| 7,571,989 B2 | 8/2009 | Ishizaki | |
| 7,798,591 B2 | 9/2010 | Ishizaki | |
| 2002/0054311 A1* | 5/2002 | Kubo | 358/1.13 |
| 2010/0118078 A1 | 5/2010 | Oshima et al. | |
| 2010/0220133 A1* | 9/2010 | Oshima et al. | 347/10 |
| 2011/0242172 A1* | 10/2011 | Yoshino et al. | 347/10 |

FOREIGN PATENT DOCUMENTS

| | | |
|---|---|---|
| JP | 2000-238262 A | 9/2000 |
| JP | 2005-329710 A | 12/2005 |
| JP | 2007-168172 A | 7/2007 |
| JP | 2007-190708 A | 8/2007 |
| JP | 2008-049698 A | 3/2008 |
| JP | 2009-153272 A | 7/2009 |
| JP | 2012-116098 A | 6/2012 |
| JP | 2013-039692 A | 2/2013 |

* cited by examiner

*Primary Examiner* — Manish S Shah
*Assistant Examiner* — Jeffrey C Morgan
(74) *Attorney, Agent, or Firm* — Maschoff Brennan

(57) ABSTRACT

A liquid ejecting device includes a driving waveform signal generating circuit that generates a driving waveform signal, a modulation circuit that performs pulse modulation on the driving waveform signal to generate a modulation signal, a digital power amplifier that amplifies power of the modulation signal to generate a power amplification modulation signal in the form of a pulse wave, a filter that smoothes the power amplification modulation signal in the pulse wave to generate the driving signal, a connection cable that connects the filter to the capacitive load and is provided such that at least one of the filter and the capacitive load is detachable, a connection line information acquiring unit that acquires connection line information associated with the connection cable, and a frequency changing unit that changes a frequency when the modulation circuit performs the pulse modulation on the driving waveform signal, on the basis of the connection line.

7 Claims, 12 Drawing Sheets

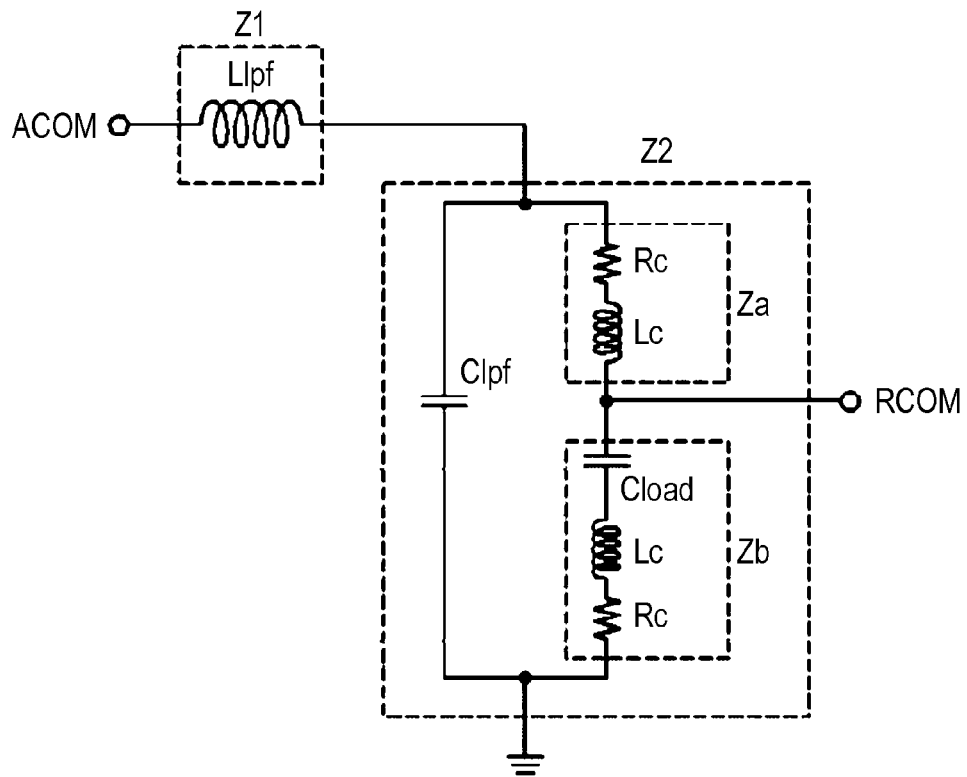

FIG. 3A $$H = \frac{Z2}{Z1+Z2} \cdot \frac{Zb}{Za+Zb} \quad \cdots\cdots (1)$$

$$H = A + jB \quad \cdots\cdots\cdots (2)$$

$$|H| = 20 \cdot \log\left(\sqrt{A^2 + B^2}\right) \quad [dB] \cdots (3)$$

WHERE $$Z1 = j\omega \cdot Llpf$$

$$Z2 = \left(\frac{1}{j\omega \cdot Clpf}\right) // \left(2(Rc + j\omega \cdot Lc) + \frac{1}{j\omega \cdot Cload}\right)$$

$$Za = Rc + j\omega \cdot Lc$$

$$Zb = Rc + j\omega \cdot Lc + \frac{1}{j\omega \cdot Cload}$$

FIG. 3B

| CONNECTED CABLE | CONNECTION LINE INFORMATION | CARRIER FREQUENCY |
|---|---|---|
| x(m) | 0 | fcx1 |
| 2x(m) | 1 | fcx2 |
| 4x(m) | 1 | fcx2 |

FIG. 7

| CONNECTED CABLE | CONNECTION LINE INFORMATION (UPPER ORDER BIT) | CONNECTION LINE INFORMATION (LOWER ORDER BIT) | CARRIER FREQUENCY |
|---|---|---|---|
| x (m) | 0 | 0 | fcx1 |
| 2x (m) | 0 | 1 | fcx3 |
| 4x (m) | 1 | 0 | fcx2 |

LIQUID EJECTING DEVICE

BACKGROUND

1. Technical Field

The present invention relates to a driving technique using a driving signal in a capacitive load such as a piezoelectric element.

2. Related Art

A technique of ejecting a fluid in a pulse to perform cutting or excision of a target is known. For example, in the medical field, as a liquid ejecting device as a surgical tool for cutting or excising a living tissue, it is known that a fluid chamber, a volume of which is changed by driving a volume changing unit, and a nozzle communicating with the fluid chamber are provided, and the fluid is converted into a pulse flow and ejected from the nozzle in a pulse at high speed by supplying the fluid to the fluid chamber and driving the volume changing unit. As an example of the volume changing unit described above, there is an actuator configured by a capacitive load such as a piezoelectric element and operated by applying a driving signal.

In addition, there are a lot of actuators configured by a capacitive load such as a piezoelectric element and operated by applying a driving signal, such as an ejection head mounted on an ink jet printer. To generate the driving signal using an analog amplification circuit, high power is consumed since there is a large electric current flow in the analog amplification circuit. As a result, not only does the power efficiency decrease, but also a circuit board becomes large, the consumed power is changed to heat so a large heat radiation plate is necessary, and the size of the board increases more and more.

A technique is proposed in which the analog driving signal is not directly amplified, a driving waveform signal that is a driving signal reference is subjected to pulse modulation and is converted into a modulation signal, the obtained modulation signal is amplified and then allowed to pass through a low pass filter, to obtain the amplified driving signal (for example, see JP-A-2007-168172). The amplification of the modulation signal may be realized only by switching the ON/OFF switch. The low pass filter may be realized using an LC circuit formed by combining a coil and a capacitor, and thus in principle power is not consumed. For this reason, according to the proposed technique, it is possible to generate the driving signal without consuming high power, and it is possible to miniaturize the circuit board.

In the proposed technique, the low pass filter is configured by the LC circuit, and thus a gain becomes a peak at a resonance frequency of the LC circuit. Generally, the output peak is suppressed by a resistance value of an electrical load or by separately inserting a damping resistor. However, in this method, power is consumed by the resistor. It is proposed that a feedback from an output stage is performed to suppress an output peak (for example, see JP-A-2009-153272). Since a phase of the signal passing through the low pass filter is delayed to the maximal 180°, the output may oscillate when the feedback is performed with the signal of the output stage as it is. The feedback is performed after performing phase lead compensation on the signal of the output stage.

A technique (see JP-A-2005-329710) of performing feedback considering connection line resistance to prevent an operation of the driving circuit from being unstable by an influence of resistance of a connection line from the low pass filter to the capacitive load when the feedback of the signal from the output stage is performed, or a technique (see JP-A-2007-190708) of switching a carrier frequency at the time of pulse modulation according to a waveform of a driving signal to suppress power consumption is proposed.

In the related art of JP-A-2007-168172, JP-A2009-153272, JP-A-2005-329710, and JP-A-2007-190708 described above, there is a problem that a ripple (carrier ripple) of the carrier frequency removed by the low pass filter may be superimposed on the driving signal. For this reason, it is difficult to appropriately drive the actuator that is the capacitive load, particularly, it is very necessary to adjust a depth and a direction of excision in the medical field, and thus it is not allowed that a small ripple (carrier ripple) of the carrier frequency is superimposed on the driving signal.

SUMMARY

An advantage of some aspects of the invention is to provide a technique capable of avoiding that a ripple of a carrier frequency is superimposed on a driving signal after passing through a low pass filter.

Application Example 1

This application example of the invention is directed to a liquid ejecting device including: an ejection unit that has a nozzle, a liquid chamber connected to the nozzle and having a variable volume, and a liquid communication pipe communicating the nozzle with the liquid chamber; a capacitive load that extends by a driving signal application and changes a volume of the liquid chamber; and a capacitive load driving circuit that drives the capacitive load by the driving signal application, wherein a liquid flowing into the liquid chamber is ejected from the nozzle by changing the volume of the liquid chamber, and wherein the capacitive load driving circuit includes a driving waveform signal generating circuit that generates a driving waveform signal that is a driving signal reference, a modulation circuit that performs pulse modulation on the driving waveform signal to generate a modulation signal, a digital power amplifier that amplifies power of the modulation signal to generate a power amplification modulation signal in the form of a pulse wave, a low pass filter that smoothes the power amplification modulation signal in the pulse wave to generate the driving signal, a connection cable that connects the low pass filter to the capacitive load and is provided such that at least one of the low pass filter and the capacitive load is detachable, a connection line information acquiring unit that acquires connection line information associated with the connection cable, and a carrier frequency changing unit that changes a carrier frequency when the modulation circuit performs the pulse modulation on the driving waveform signal, on the basis of the connection line information.

According to this application example, the modulation signal is generated by performing the pulse modulation on the driving waveform signal that is the driving signal reference to be applied to the capacitive load, and the obtained modulation signal is subjected to power amplification and then is smoothed, thereby generating the driving signal. Phase lead compensation is performed on the driving signal applied to the capacitive load as described above to generate a feedback signal, and negative feedback to the driving waveform signal is performed. The low pass filter is connected to the capacitive load by the connection cable, and the driving signal output from the low pass filter is applied to the capacitive load through the connection cable. The connection cable is detachable, the connection line information about the connection cable is acquired when the low pass filter is connected to the capacitive load by the connection cable, and the pulse modulation is performed at the carrier frequency corresponding to the connection line information.

In the driving waveform signal that is the driving signal reference, the negative feedback of the driving signal applied to the capacitive load is performed, and thus it is possible to prevent the driving signal from being distorted by the influence of resonance of the low pass filter. When the negative feedback of the driving signal is performed, the negative feedback is performed after performing the compensation (phase lead compensation) to advance the phase. Accordingly, the output of the driving signal is prevented from being unstable due to the negative feedback of the phase-delayed driving signal by the low pass filter. Although details thereof will be described later, a frequency at which the carrier ripple is easily superimposed is determined by the connection cable. Accordingly, when the information about the frequency at which the carrier ripple is easily superimposed is stored as the connection line information, the connection line information of the connected connection cable is acquired and the pulse modulation is performed at the carrier frequency avoiding the frequency with which the carrier ripple is easily superimposed. As a result, it is possible to avoid that the carrier ripple is superimposed on the driving signal, and thus it is possible to provide a medical apparatus with high stability and high resection performance.

Application Example 2

This application example is directed to the liquid ejecting device according to the above application example, wherein the connection line information is information associated with an inductance value or an impedance value of the connection cable.

According to this application example, the frequency with which the carrier ripple is easily superimposed may be strongly affected by the magnitude of the inductance component or the impedance of the connection cable. Accordingly, when the information associated with the magnitude of the inductance component or the impedance of the connection cable is acquired as the connection line information, it is possible to perform the pulse modulation at the carrier frequency avoiding the frequency with which the carrier ripple is easily superimposed, and thus it is possible to avoid that the carrier ripple is superimposed on the driving signal.

Application Example 3

This application example is directed to the liquid ejecting device according to the above application example, wherein the connection line information is information associated with a length of the connection cable.

According to this application example, the magnitude of the inductance component of the connection cable significantly depends on the length of the connection cable. Accordingly, when the information associated with the length of the connection cable is stored as the connection line information, the pulse modulation is performed at the carrier frequency avoiding the frequency with which the carrier ripple is easily superimposed, and it is possible to avoid that the carrier ripple is superimposed on the driving signal.

Application Example 4

This application example is directed to the liquid ejecting device according to the above application example, wherein at least a connector of the connection cable on the low pass filter side is provided with a protruding terminal to which the driving signal is transferred from the low pass filter, and the connection line information acquiring unit detects whether or not the connector is provided with the protruding terminal to which the driving signal is not transferred, thereby acquiring the connection line information.

In other words, at least the connector of the connection cable on the low pass filter side is provided with the protruding terminal, and the driving signal from the low pass filter is transferred through the terminal when the connection cable is connected. The connection may be provided with the protruding terminal which is not included in the transfer of the driving signal, and the connection line information acquiring unit may detect whether or not the connection is provided with the protruding terminal which is not included in the transfer of the driving signal, thereby acquiring the connection line information.

According to this application example, when the connection cable is connected, it is possible to select a proper carrier frequency and to perform the pulse modulation according to whether or not the connection is provided with the protruding terminal which is not included in the transfer of the driving signal. As a result, it is possible to avoid that the carrier ripple is superimposed on the driving signal.

Application Example 5

This application example is directed to the liquid ejecting device according to the above application example, wherein the terminal to which the driving signal is not transferred is configured by an optical plug in which optical fibers are combined.

According to this application example, durability is satisfactory as compared with a contact-type terminal.

Application Example 6

This application example is directed to the liquid ejecting device according to the above application example, wherein the terminal to which the driving signal is not transferred has a magnet.

According to this application example, durability is satisfactory as compared with a contact-type terminal.

Application Example 7

This application example is directed to the liquid ejecting device according to the above application example, wherein the connection cable is provided with a storage medium readably storing the connection line information, and the connection line information acquiring unit is a unit that reads the connection line information from the storage medium.

According to this application example, the connection line information is read only by connecting the connection cable, and it is possible to perform the pulse modulation at the carrier frequency avoiding the frequency with which the carrier ripple is easily superimposed. As a result, it is possible to avoid that the carrier ripple is superimposed on the driving signal.

Application Example 8

This application example is directed to the liquid ejecting device according to the above application example, wherein the connection cable is provided with an ID tag in which the connection line information is recorded.

According to this application example, an operator of the capacitive load driving circuit reads the connection line information recorded in the ID tag and acquires the connection line information, and thus it is possible to perform the pulse modulation at the carrier frequency avoiding the frequency with which the carrier ripple is easily superimposed. As a result, it is possible to avoid that the carrier ripple is superimposed on the driving signal.

BRIEF DESCRIPTION OF THE DRAWINGS

The invention will be described with reference to the accompanying drawings, wherein like numbers reference like elements.

FIG. 3A is a diagram illustrating a transfer function H. FIG. 3B is a diagram illustrating a mechanism in which a carrier ripple occurs by an influence of an inductance component (and a resistance component) of a connection cable.

FIG. 7 is a diagram illustrating that a carrier frequency is changed according to connection line information.

DESCRIPTION OF EXEMPLARY EMBODIMENTS

Hereinafter, to clarify the contents of the invention described above, embodiments will be described in the following order.
A. Device Configuration
B. Circuit Configuration of Capacitive load Driving Circuit
C. Mechanism of Generation of Carrier Ripple
D. Capacitive load Driving Circuit of First Example
E. Capacitive load Driving Circuit of Second Example
F. Capacitive load Driving Circuit of Third Example
G. Liquid Ejection Type Printing Apparatus (Printer)

A. Device Configuration

Figure 1:
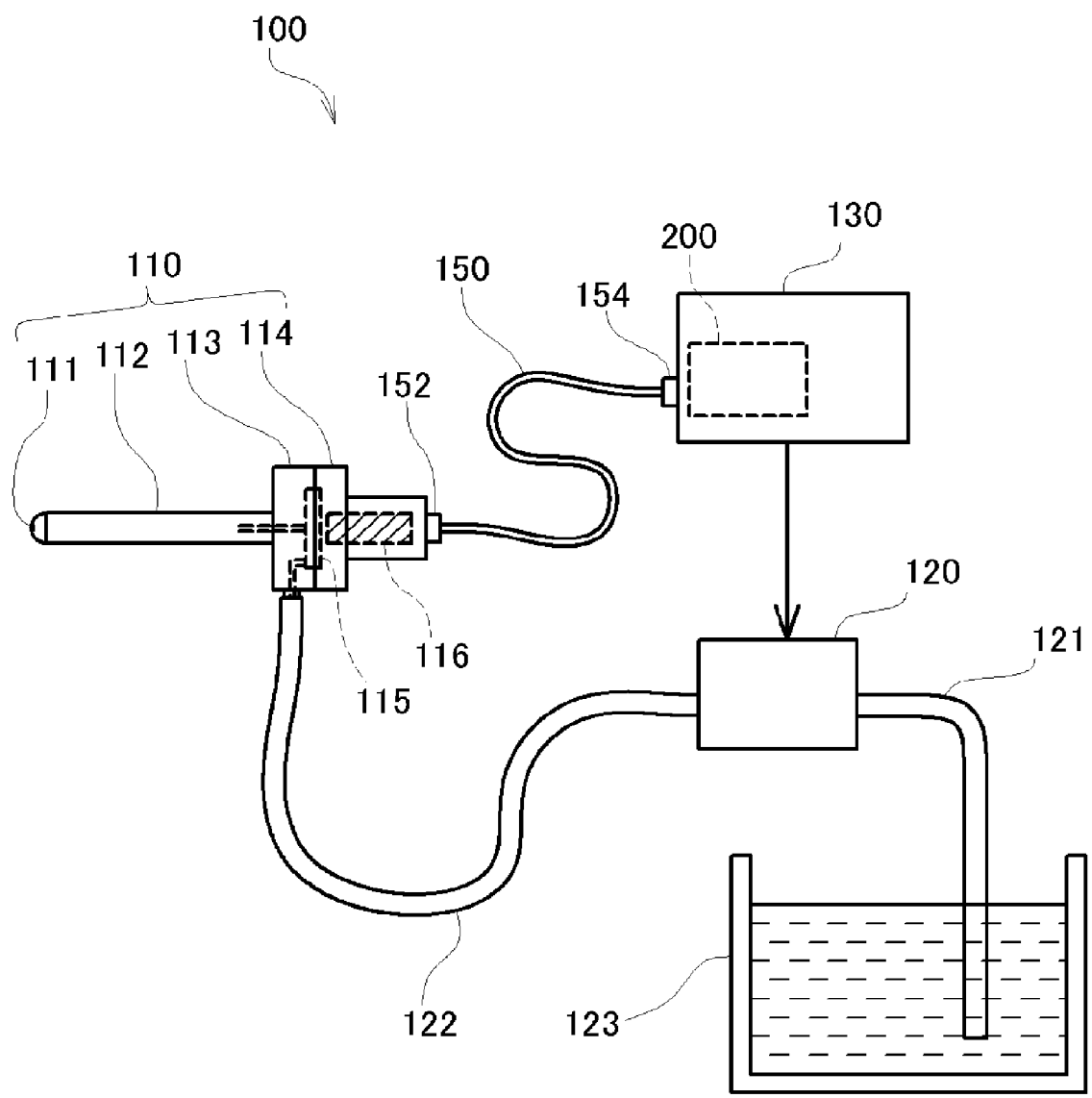
FIG. 1 is a diagram illustrating a configuration of a liquid ejecting device provided with a capacitive load driving circuit according to an embodiment.

FIG. 1 is a diagram illustrating a configuration of a liquid ejecting device provided with a capacitive load driving circuit according to an embodiment. As shown in FIG. 1, a liquid ejecting device 100 mainly includes an ejection unit 110 that ejects a liquid, a supply pump 120 that supplies the liquid ejected from the ejection unit 110, toward the ejection unit 110, and a control unit 130 that controls operations of the ejection unit 110 and the supply pump 120. The liquid ejecting device 100 is an example of a water jet scalpel as a surgical tool used to cut or excise a living tissue by ejecting the liquid in a pulse from the ejection unit 110.

The ejection unit 110 has a structure in which a front block 113 formed of metal is superimposed on and fixed to a rear block 114 formed of the same metal by screws, a liquid passage pipe 112 having a circular pipe shape is provided to be erect on the front face of the front block 113, an ejection nozzle 111 is inserted and attached to the leading end of the liquid passage pipe 112. A liquid chamber 115 in a thin disc shape is formed on a joint face of the front block 113 and the rear block 114, and the liquid chamber 115 is connected to the ejection nozzle 111 through the liquid passage pipe 112. The rear block 114 is provided therein with an actuator 116 configured by a lamination-type piezoelectric element. The ejection unit 110 is connected to the control unit 130 by a connection cable 150, and a driving signal is supplied from a capacitive load driving circuit 200 in the control unit 130 to the actuator 116 through the connection cable 150. One end side of the connection cable 150 is connected to the ejection unit 110 by a connector 152, and the other end side of the connection cable 150 is connected to the control unit 130 by a connector 154. For this reason, the connection cable 150 may be changed to various connection cables 150 with different lengths and characteristics. The actuator 116 corresponds to the "capacitive load" in the invention.

The supply pump 120 pumps up the liquid from a liquid tank 123 collecting the liquid (water, physiological saline, liquid medicine, or the like) to be ejected, through a tube 121, and then supplies the liquid into the liquid chamber 115 of the ejection unit 110 through a tube 122. For this reason, the liquid chamber 115 is filled with the liquid.

When the driving signal is applied from the control unit 130 to the actuator 116, the actuator 116 is stretched to contract the liquid chamber 115. As a result, the liquid filled in the liquid chamber 115 is ejected in pulse from the ejection nozzle 111. The stretch amount of the actuator 116 depends on voltage applied as the driving signal. Accordingly, to eject the liquid in the pulse with desired characteristics, it is necessary to apply a driving signal with high precision to the actuator 116. To generate such a driving signal, the control unit 130 is provided therein with the capacitive load driving circuit 200 to be described hereinafter.

B. Circuit Configuration of Capacitive Load Driving Circuit

Figure 2:
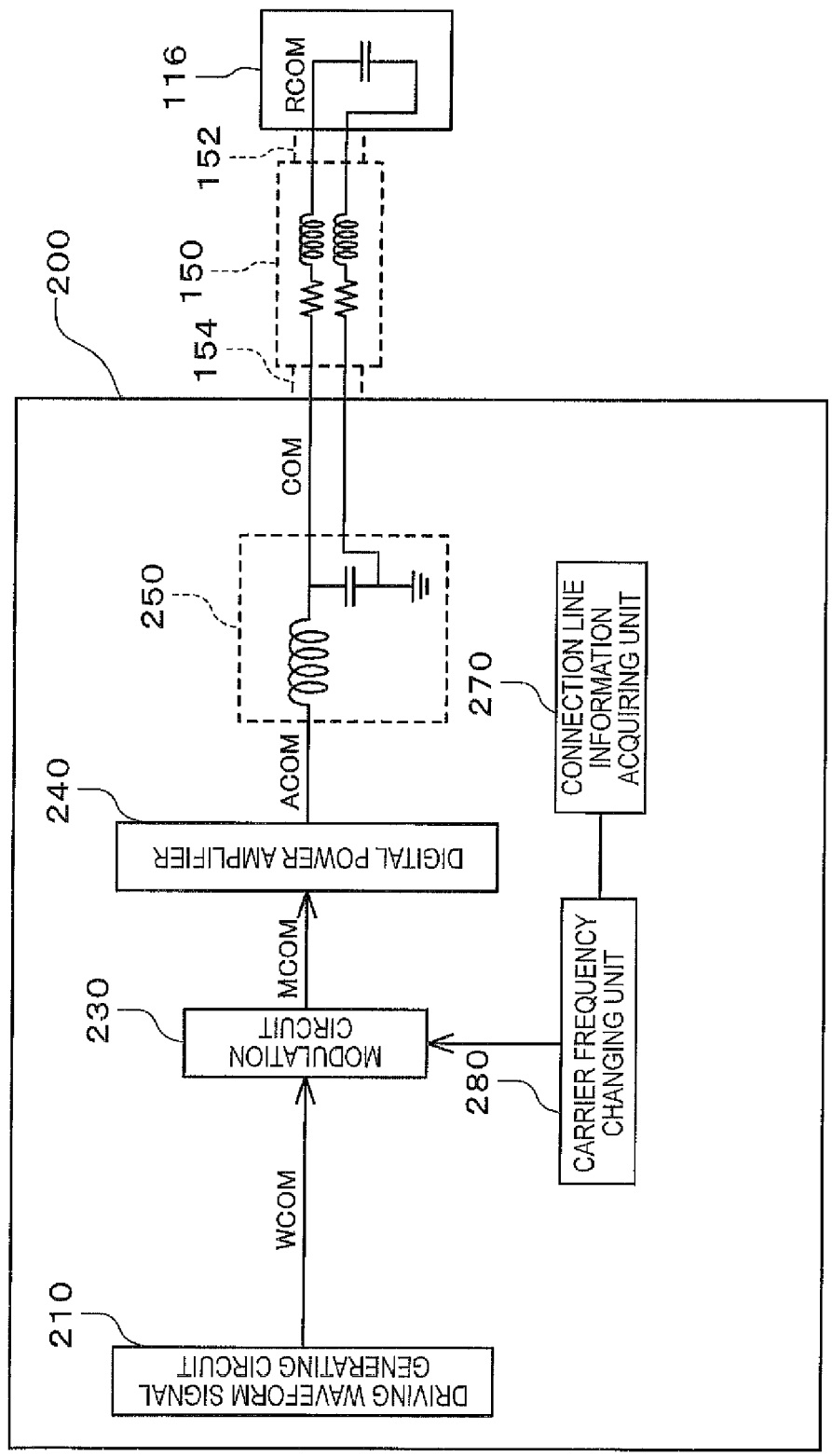
FIG. 2 is a diagram illustrating a circuit configuration of the capacitive load driving circuit according to the embodiment.

FIG. 2 is a diagram illustrating a circuit configuration of the capacitive load driving circuit 200 according to the embodiment. As shown in FIG. 2, the capacitive load driving circuit 200 includes a driving waveform signal generating circuit 210 that outputs a driving waveform signal (hereinafter, referred to as WCOM) that is a driving signal reference, a modulation circuit 230 that performs pulse modulation on the WCOM from the driving waveform signal generating circuit 210 and converts it into a modulation signal (hereinafter, referred to as MCOM), a digital power amplifier 240 that digitally amplifies power of the MCOM from the modulation circuit 230 and generates a power amplification modulation signal (hereinafter, referred to as ACOM), and a low pass filter 250 that receives the ACOM from the digital power amplifier 240, removes a modulation component therefrom, and then supplies the signal as a driving signal (hereinafter, referred to as COM) to the actuator 116 of the ejection unit 110.

Among them, the driving waveform signal generating circuit 210 is provided with a waveform memory storing data of the WCOM and a D/A converter, and generates the WCOM (driving waveform signal) by converting the data read from the waveform memory into an analog signal by the D/A converter. On the contrary, the modulation circuit 230 is configured by a digital circuit using a signal processing circuit, and the WCOM (driving waveform signal) read from the waveform memory of the driving waveform signal generating circuit 210 may be considered as digital data.

The modulation circuit 230 generates (pulse modulation) the MCOM (modulation signal) as a pulse wave by comparing the WCOM with a triangular wave of a regular cycle. Herein, a base frequency (carrier frequency) of the triangular wave used in the pulse modulation is changeable by a control of a carrier frequency changing unit 280. The carrier frequency changing unit 280 changes the carrier frequency on the basis of the connection line information (information about the connection cable 150 connecting the ejection unit 110 to the control unit 130) acquired by a connection line information acquiring unit 270. Although details thereof will be described later, it is possible to avoid that the carrier ripple is superimposed on the COM by changing the carrier frequency at the time of the pulse modulation on the basis of the connection line information as described above.

The MCOM obtained by the modulation circuit 230 is input to the digital power amplifier 240. The digital power amplifier 240 includes two push-pull connected switch elements (MOSFET and the like), a power supply, and a gate driver that drives the switch elements. In the example, the voltage of the power supply described above is Vdd [V]. When the MCOM is in a high level state, the switch element on the high side is turned on, the switch element on the low side is turned off, and the voltage Vdd of the power supply is output as the ACOM. When the MCOM is in a low level state, the switch element on the high side is turned off, the switch element on the low side is turned on, and the ground voltage is output as the ACOM. As a result, the power of the MCOM changed in the pulse wave between the operation voltage of the modulation circuit 230 and the ground is amplified to the ACOM changed in the pulse wave between the voltage Vdd of the power supply and the ground. In the amplification, the ON/OFF of the two push-pull connected switch elements are switched, and thus it is possible to drastically suppress power loss as compared with the case of amplifying the analog waveform. As a result, it is possible to improve the power efficiency, it is not necessary to provide a large heat sink for heat radiation, and thus it is possible to miniaturize the circuit.

The ACOM (power amplification modulation signal) amplified as described above passes through the low pass filter 250 configured by the LC circuit to be converted into the COM (driving signal), and is applied to the actuator 116 through the connection cable 150. The detailed configuration of the connection line information acquiring unit 270 will be described later.

As shown in FIG. 2, the connection cable 150 described above also has the inductance component and the resistance component. Accordingly, by this influence, it is considered that any deviation occurs between the COM output from the low pass filter 250 and the signal (hereinafter, referred to as RCOM) actually applied to the actuator 116. Actually trying to study, according to the length and kind of the connection cable 150 or the magnitude of the inductance component of the connection cable 150 (and the resistance component) determined thereby, it was found that the carrier ripple may be superimposed on the RCOM actually applied to the actuator 116. The carrier ripple means a signal component, which is included in the RCOM applied to the actuator 116, of the carrier signal (triangular signal) used in the pulse modulation. Hereinafter, this point will be described in detail.

C. Mechanism of Generation of Carrier Ripple

When the reason why the carrier ripple described above can be superimposed is described, first, it is necessary to describe a transfer function (hereinafter, represented by H) when the ACOM is the input signal and the RCOM is the output signal. Constituent elements of the transfer function H may be the low pass filter 250, the connection cable 150, and the actuator 116 that is the capacitive load. Various circuit models are conceivable about the connection cable 150. However, in the example, as shown in FIG. 2, a circuit model including an inductance component and a resistance component will be described as an example. FIG. 3A and FIG. 3B are diagrams illustrating the transfer function H described above. FIG. 3A shows a circuit configuration from the ACOM to the ROOM. The inductance of the coil of the low pass filter 250 is Llpf [H], and a capacitance of the capacitance component of the low pass filter 250 is Clpf [F]. Similarly, the resistance value and the inductance of the connection line on one side are Rc [Ω] and Lc [H], respectively. A capacitance of the capacitive load is Cload [F].

For convenience, as shown in FIG. 3A and FIG. 3B, Z1, Za, and Zb are given in the following formula, when the impedance of the coil of the low pass filter 250 is Z1, the impedance on the going side (the side of transmission from the low pass filter 250 to the actuator 116) of the connection cable 150 is Za, and the impedance of the part in which the returning side (the side of returning from the actuator 116 to the ground of the capacitive load driving circuit 200) of the connection cable 150 is added to the actuator 116 is Zb.

$$Z1 = j\overline{\omega} \cdot Llpf$$

$$Za = Rc + j\overline{\omega} \cdot Lc$$

$$Zb = 1/(j\overline{\omega} \cdot Cload) + (Rc + j\overline{\omega} \cdot Lc)$$

In the circuit configuration shown in FIG. 3A, an impedance Z2 of the transfer element (capacitance component of the low pass filter 250, the actuator 116, and the going and returning part of the connection cable 150) connected in series to the coil of the low pass filter 250 is given in the following formula.

$$Z2 = \{1/(j\overline{\omega} \cdot Clpf)\} // \{2(Rc + j\overline{\omega} \cdot Lc) + 1/(j\overline{\omega} \cdot Cload)\}$$

In the formula, $\overline{\omega}$ is an angular frequency, and is obtained by multiplying the frequency f by $2\pi$. In addition, j is the imaginary number unit. In addition, // is a parallel synthetic symbol representing synthetic impedance of parallel connection. Then, the transfer function H between the ACOM and the RCOM is given in formula (1) shown in FIG. 3B.

In formula (1) shown in FIG. 3B, to avoid complexity of representation of the formula, the transfer function H is represented by the impedances Z1, Z2, Za, and Zb. However, as described above, the impedances Z1, Z2, Za, and Zb are represented by the angular frequency $\overline{\omega}$ (or frequency f) or the inductance component Lc of the connection cable 150. Accordingly, when the transfer function H shown in formula (1) is developed, it may be represented in the form of formula (2) shown in FIG. 3B by the formulas A and B including the angular frequency $\overline{\omega}$ (or frequency f), the inductance component Lc of the connection cable 150, or the resistance component Rc.

A gain |H| [dB] of the transfer function H is represented in formula (3) shown in FIG. 3B. Similarly to formula (2), formula (3) includes the angular frequency $\overline{\omega}$ (or frequency f), and thus the gain |H| of the transfer function H is a parameter that changes depending on the frequency.

The description of the transfer function H has been given above. Next, to describe why the carrier ripple described above can be superimposed, a relationship between gain |H|-frequency characteristics of the transfer function H and the carrier ripple will be described.

Figure 4:
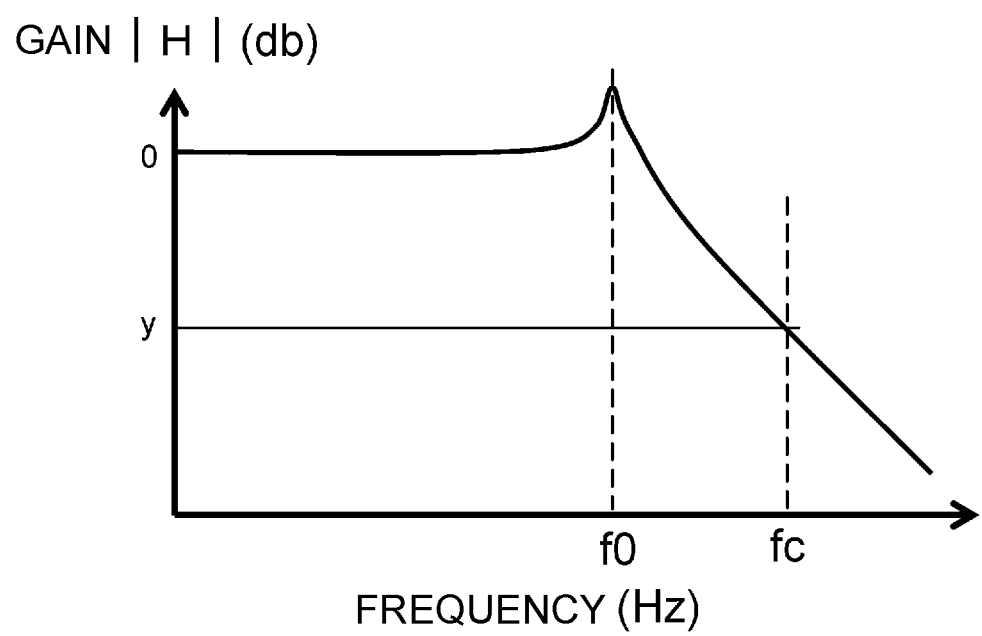
FIG. 4 is a diagram illustrating a mechanism in which a carrier ripple occurs by an influence of an inductance component (and a resistance component) of a connection cable.

FIG. 4 shows an example of the gain |H|-frequency characteristics of the transfer function H when there is no connection cable 150 (cable length is 0 m). As described above, the carrier frequency fc is a fixed constant frequency. In FIG. 4, when there is no connection cable 150, the gain in the carrier frequency fc is y [dB]. When the power supply voltage of the digital power amplifier 240 described above is Vdd [V], the carrier ripple Vrpp [Vpp] superimposed on the RCOM is represented in formula (4) shown in FIG. 4. However, formula (4) is a carrier ripple when a duty ratio of the pulse modulation signal described above is 50%.

From formula (4), for example, the carrier ripple superimposed on the RCOM is calculated as 1 Vpp, when the power supply voltage of the digital power amplifier 240 is 100 V and the gain y shown in FIG. 4 is −40 [dB].

Meanwhile, a case where there is the connection cable 150 is considered.

Figure 5:
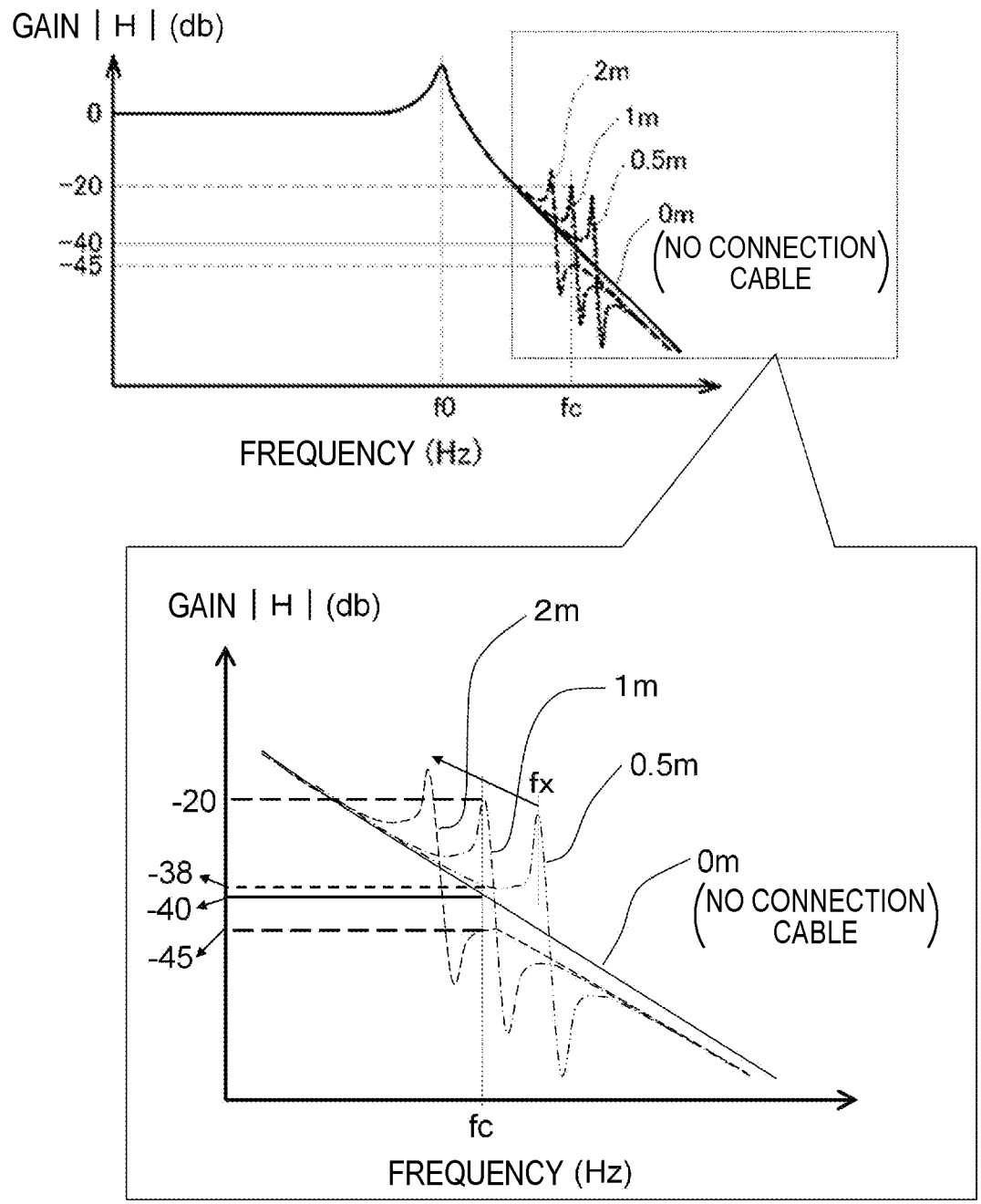
FIG. 5 is a diagram illustrating a mechanism in which a carrier ripple occurs by an influence of an inductance component (and a resistance component) of a connection cable.

Similarly to formula (2) described above, formula (3) includes the inductance component Lc and the resistance component Rc of the connection cable 150. Accordingly, when there is the connection cable 150 and may be changed to a connection cable 150 with a different length or kind, the inductance component Lc and the resistance component Rc of the connection cable 150 are changed, and thus the gain |H|-frequency characteristics of the transfer function H are changed. FIG. 5 shows an example of the gain |H|-frequency characteristics of the transfer function H. In FIG. 5, it is assumed that the resistance component Rc in a unit length of the connection cable 150 is about several hundred milli Ω and the inductance component Lc in a unit length is about several μH, and the gain-frequency characteristics obtained by various connection line lengths are exemplified.

The broken line shown in FIG. 5 is the gain-frequency characteristics when the length of the connection cable 150 is 2 [m (meter)], the chain line is the gain-frequency characteristics when the length is 1 [m], and the two-dot chain line is the gain-frequency characteristics when the length is 0.5 [m]. The solid line represents the gain-frequency characteristics when there is no connection cable 150. As shown in FIG. 5, when the actuator 116 (capacitive load) is connected through the connection cable 150, resonance of the frequency fx occurs on the higher frequency side than the resonance frequency f0 of the low pass filter 250 from the relationship of formula (3) (the gain |H| of the transfer function). When the connection cable 150 may be changed to a longer cable, the inductance value of the connection cable 150 becomes larger, and thus the resonance frequency fx described above becomes lower from the relationship of formula (3). Accordingly, similarly to the case where the length of the connection cable 150 shown in FIG. 5 is 1 m, the resonance peak of the frequency fx approaches or coincides with the carrier frequency fc, according to the length (or the inductance determined by the length) of the connected connection cable 150. As a result, the gain in the carrier frequency fc becomes large, and thus a very large carrier ripple may remain in the driving signal applied to the actuator 116 from the relationship shown in formula (3).

Referring to FIG. 5, it will be described how much the magnitude of the carrier ripple is changed according to whether or not there is the connection cable 150 and by the length of the connected connection cable 150. The power supply voltage Vdd of the digital power amplifier 240 is 100 V. As the connection cable 150 connecting the low pass filter 250 to the actuator 116, cables with various lengths from 0.5 [m] to 2 [m] are connected. From FIG. 5, in a case where there is no connection cable 150 (0 [m]), a case where the cable length of the connection cable 150 is 0.5 [m], a case where the cable length is 1 [m], and a case where the cable length is 2 [m], the gain in the carrier frequency fc is −40 dB, −38 dB, −20 dB, and −45 dB respectively. From formula (4), the carrier ripple remaining in the driving signal is 1 Vpp, 1.25 Vpp, 10 Vpp, and 0.56 Vpp respectively. Accordingly, in the embodiment, when the connection cable may be changed to the connection cable 150 with the length of 1 [m], the gain in the carrier frequency fc becomes large, and a very large carrier ripple of 10 Vpp may remain in the driving signal applied to the actuator 116. In spite of smoothing the ACOM amplified by the digital power amplifier 240 through the low pass filter 250, it is considered that the carrier ripple is superimposed on the driving signal by the mechanism described above.

By the overlapping of the carrier ripple, it is difficult to appropriately drive the actuator 116. Particularly, it is directly connected to difficulty of the adjustment of the depth or the direction of cutting in medical field, and thus such a phenomenon is not allowed. However, when the damping resistor is inserted to the connection line, power is consumed by the resistor, and thus power efficiency is decreased. When the characteristics of the low pass filter 250 are changed to further suppress the frequency component of the carrier ripple, the resonance frequency f0 of the low pass filter 250 is decreased, and thus it is difficult to secure a band of a signal frequency. On the contrary, when the carrier frequency at the time of the pulse modulation is sufficiently high, it is possible to suppress the carrier ripple, but a switching loss at the time of the pulse modulation or the amplification of the modulation signal is increased. To apply the driving signal with no carrier ripple to the actuator 116 without such a problem, the following method is employed.

D. Capacitive Load Driving Circuit of First Example

Figure 6:
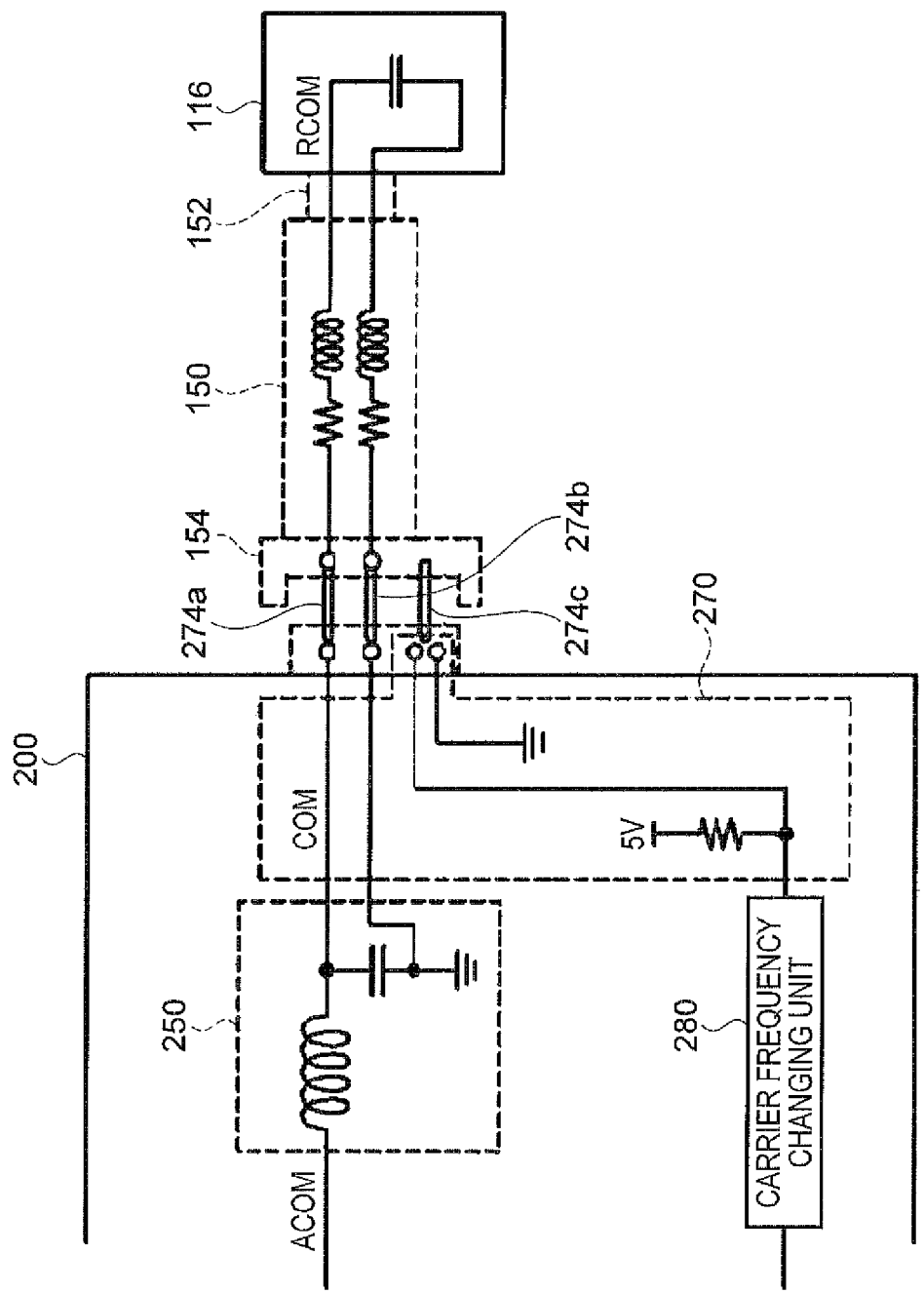
FIG. 6 is a circuit diagram illustrating a part of a capacitive load driving circuit according to a first example.

FIG. 6 is a circuit diagram illustrating a part of the capacitive load driving circuit 200 of the example. Specifically, the carrier frequency corresponding to the connection line information is set by connecting the connection cable 150. In the example, the connector 154 connected to the connection cable 150 on the control unit 130 side (the capacitive load driving circuit 200 side) is a male connector, and the connector on the control unit 130 side (the capacitive load driving circuit 200 side) is a female connector. The connector 154 on the connection cable 150 is provided with a terminal 274a and a terminal 274b to be erect. When the connection cable 150 is connected to the control unit 130 (the capacitive load driving circuit 200), the terminal 274a is connected to the line of the COM output from the low pass filter 250, and the terminal 274b is connected to the ground line.

As shown in FIG. 6, in the example, the connector 154 of the connection cable 150 on the control unit 130 (the capacitive load driving circuit 200) side is also provided with one terminal 274c. When the connection cable 150 is connected to the control unit 130 (the capacitive load driving circuit 200), the terminal 274c short-circuits the contact point as the connection line information acquiring unit provided on the capacitive load driving circuit 200. That is, when the connector 154 is provided with the terminal 274c, the contact point of the capacitive load driving circuit 200 is short-circuited. When the terminal 274c is not provided, the contact point of the capacitive load driving circuit 200 is cut off. Accordingly, the connection line information may be stored according to whether or not the connector 154 of the connection cable 150 is provided with the terminal 274c. In the example, the terminal 274c in the connector 154 corresponds to the "connection line information acquiring unit" according to the invention.

In the carrier frequency changing unit 280, the connection line information is detected by the contact point state when the connection cable 150 is connected. FIG. 7 is a diagram illustrating that the carrier frequency is changed according to the connection line information described above. In FIG. 7, it is assumed that the connection line information is in a "1" state, when the connector 154 is not provided with the terminal 274c and the contact point is cut off. It is assumed that the connection line information is in a "0" state, when the connector 154 is provided with the terminal 274c and the contact point is short-circuited.

In FIG. 7, it is assumed that the length of the connection cable 150 is described as the connection line information. For example, when the cable length that is the connection line information is x [m (meter)], the connector 154 of the connection cable 150 is provided with the terminal 274c (connection line information="0"). Then, the carrier frequency fcx1 is selected by the carrier frequency changing unit 280. When the cable length that is the connection line information is 2x [m] or 4x [m], the connector 154 of the connection cable 150 is not provided with the terminal 274c (connection line information="1"), and the carrier frequency fcx2 is selected. In such a manner, it is possible to avoid that the carrier ripple is superimposed on the driving signal to the actuator 116, from the following reason. In FIG. 7, the cable length is described as the connection line information, but the connection line information may be a simple number or symbol. As described above, the frequency fx of the resonance generated when the connection cable 150 is mounted is changed according to the inductance value or the impedance value of the mounted connection cable. Accordingly, instead of the cable length of the connection cable 150, the carrier frequency may be set with respect to the inductance value or the impedance value of the connection cable.

Figure 8:
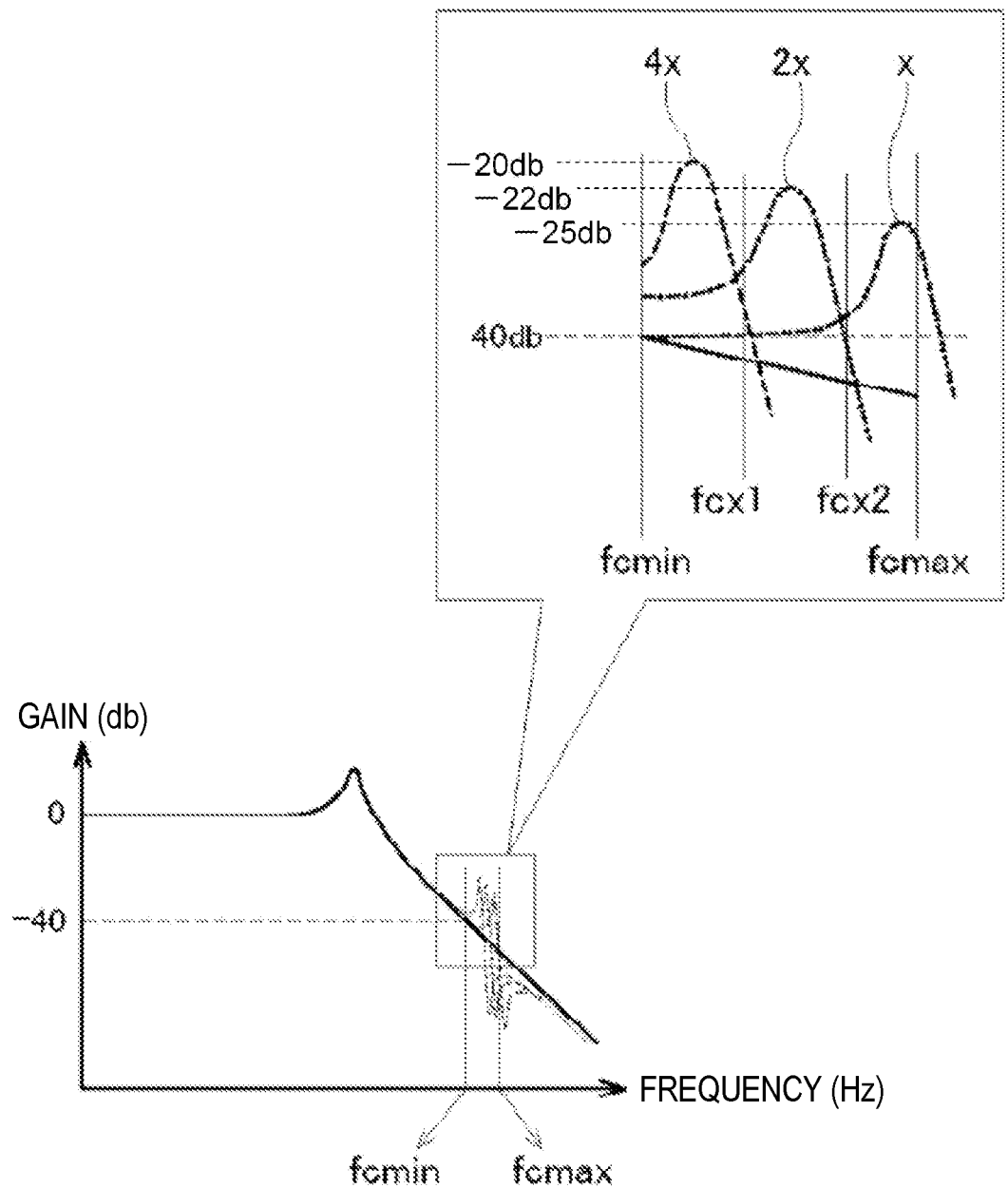
FIG. 8 is a diagram illustrating a reason why it is possible to avoid that the carrier ripple is superimposed, by changing the carrier frequency according to the connection line information.

FIG. 8 is a diagram illustrating a reason why it is possible to avoid that the carrier ripple is superimposed, by changing the carrier frequency according to the connection line information. In FIG. 8, the connection cables 150 which may be connected are three kinds of x [m], 2x [m], and 4x [m]. Then, when the connection cables 150 are used, the resonance frequency fx generated between the connection cable 150 and the actuator 116 may be examined in advance using formula (3). However, it is necessary to measure the values of the inductance components and the resistance components of the connection cables.

In FIG. 8, the gain-frequency characteristics when the connection cable 150 of x [m] is connected are represented by the two-dot chain line. The gain-frequency characteristics when the connection cable 150 of 2x [m] is connected are represented by the chain line, and the gain-frequency characteristics when the connection cable 150 of 4x [m] is connected are represented by the broken line. The resonance frequency of the low pass filter 250 is determined from a necessary signal frequency band, and it is difficult to further lower the resonance frequency. That is, it is difficult to design an attenuation amount in a high frequency area to be larger that that. In the characteristics of the low pass filter 250 determined as described above, in an ideal state where the connection cable 150 is not connected, a frequency (minimum frequency) satisfying a specification value of the carrier ripple of the application in the minimum is represented by "fcmin" in FIG. 8. From the viewpoint of suppressing the switching loss, that is, the viewpoint of preventing the breakdown caused by the heat generation of the switching element, there is a frequency at which it is difficult to further raise the carrier frequency. In FIG. 8, such a frequency (maximum frequency) is represented by "fcmax".

It is necessary to design the carrier frequency at the time of the pulse modulation between the minimum frequency fcmin and the maximum frequency fcmax. Between the minimum frequency fcmin and the maximum frequency fcmax, two kinds of carrier frequencies fcx1 and fcx2 are set at a distance from each other. In the example, when the gain in the carrier frequency is equal to or lower than −40 dB, it is considered that the carrier ripple is invisible. For example, it is thought that the power supply voltage of the digital power amplifier 240 is 100 V as described above. In this case, the carrier ripple superimposed on the RCOM is calculated as 1 Vpp, from formula (4). Accordingly, in the example, it is considered that the carrier ripple of about 1 Vpp is in a level with no problem. As described above, it is possible to calculate the gain-frequency characteristics from the length, the inductance value, or the impedance value of the connected connection cable 150 using formulas (3) and (4). Accordingly, the fcx1 is set as a frequency in which the gain is within a target value (in the example, −40 dB) when the connection cable with the length x [m] is mounted. The fcx2 is set as a frequency in which the gain is within the target value (in the example, −40 dB) when the connection cable with the length 2x [m] or 4x [m] is mounted.

As shown in FIG. 8, in the example, the gains in the resonance frequency fx generated when the connection cables 150 with the lengths x [m], 2x [m] and 4x [m] are mounted are −25 dB, −22 dB, and −20 dB, respectively. In this case, if the connection cable is a connection cable with a length (or an inductance) in which the resonance frequency fx coincides with the carrier frequency, the carrier ripples are 5.6 Vpp, 7.9 Vpp, and 10 Vpp respectively from formula (4). As clarified from FIG. 8, when the connection cable 150 with the cable length x [m] is connected and the carrier frequency is set to fcx1, it is possible to suppress the gain to −40 dB. When the connection cable 150 with the cable length 2x [m] or 4x [m] is connected and the carrier frequency is set to fcx2, it is possible to suppress the gain in the carrier frequency to −40 dB or lower. As shown in FIG. 7, the carrier frequency fcx1 or fcx2 is set according to the cable length (that is, the connection line information) of the connection cable 150. In this case, even when any connection cable 150 of x [m] to 4x [m] is connected, it is possible to avoid that the carrier ripple is superimposed on the driving signal to the actuator 116.

The minimum frequency fcmin and the maximum frequency fcmax may be set as two kinds of preset carrier frequencies fcx1 and fcx2. In the above description, the connection line information is stored according to whether or not there is one terminal 274c, thus the connection line information becomes 1-bit information, and it is possible to select any one of two kinds of carrier frequencies fcx1 and fcx2. When the connection line information is stored according to whether or not there are the terminals 274c of a plurality of lines, the number of bits of the connection line information is increased, and thus it is possible to set a proper carrier frequency among more kinds of carrier frequencies. Accordingly, more kinds (three kinds or more) of carrier frequencies are set between the minimum frequency fcmin and the maximum frequency fcmax, the carrier frequency may be set according to the connection line information of the terminal 274c.

Figures 9A, 9B:
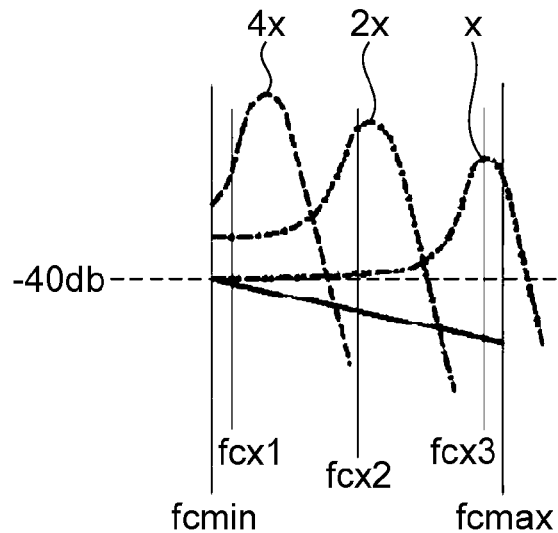
FIG. 9A and FIG. 9B are diagrams illustrating an example of the other aspect of the first example.

FIG. 9A and FIG. 9B are diagrams illustrating an example of the other aspect of the example. Specifically, the carrier frequency corresponding to the connection line information is selected from three or more kinds of carrier frequencies. FIG. 9A shows that three kinds of carrier frequencies fcx1, fcx2, and fcx3 are set between the minimum frequency fcmin and the maximum frequency fcmax. Herein, the connection line information is stored according to whether or not there are two terminals 274c (referred to as the first terminal and the second terminal). The "low order bit of connection line information" shown in FIG. 9B is determined according to whether or not there is the first terminal, and the "upper order bit of connection line information" is determined according to whether or not there is the second terminal. The correspondence between the present states of the terminal 274c and "0" and "1" of the connection information is as described above. FIG. 9B shows that any carrier frequency is selected, according to the cable length (connection line information), by the connection line information determined according to whether or not there are the first terminal and the second terminal. When the kinds of the carrier frequencies are increased as described above, it is possible to select a more proper carrier frequency according to the connected connection cable 150. From the viewpoint of suppressing the switching loss, when there are a number of frequencies with the gain of −40 dB or lower, it is preferable to set the low frequency as possible, as the carrier frequency. The terminal 274c described above may be configured by an optical plug formed by combining optical fibers, and may be formed by short-circuiting or cutting the contact point by magnetic force of a magnet.

E. Capacitive Load Driving Circuit of Second Example

In the first example described above, as the configuration example of the connection line information acquiring unit 270, the connection line information is stored according to whether or not there is the terminal 274c provided in the connector 154 of the connection cable 150. The ROM (storage medium) storing the connection line information may be provided in advance in the connector 154 of the connection cable 150 on the control unit 130 (the capacitive load driving circuit 200) side. In the second example and the third example to be described hereinafter, the same reference numerals and signs are given to the same configuration as that of the first example, and the description thereof is not repeated.

Figure 10:
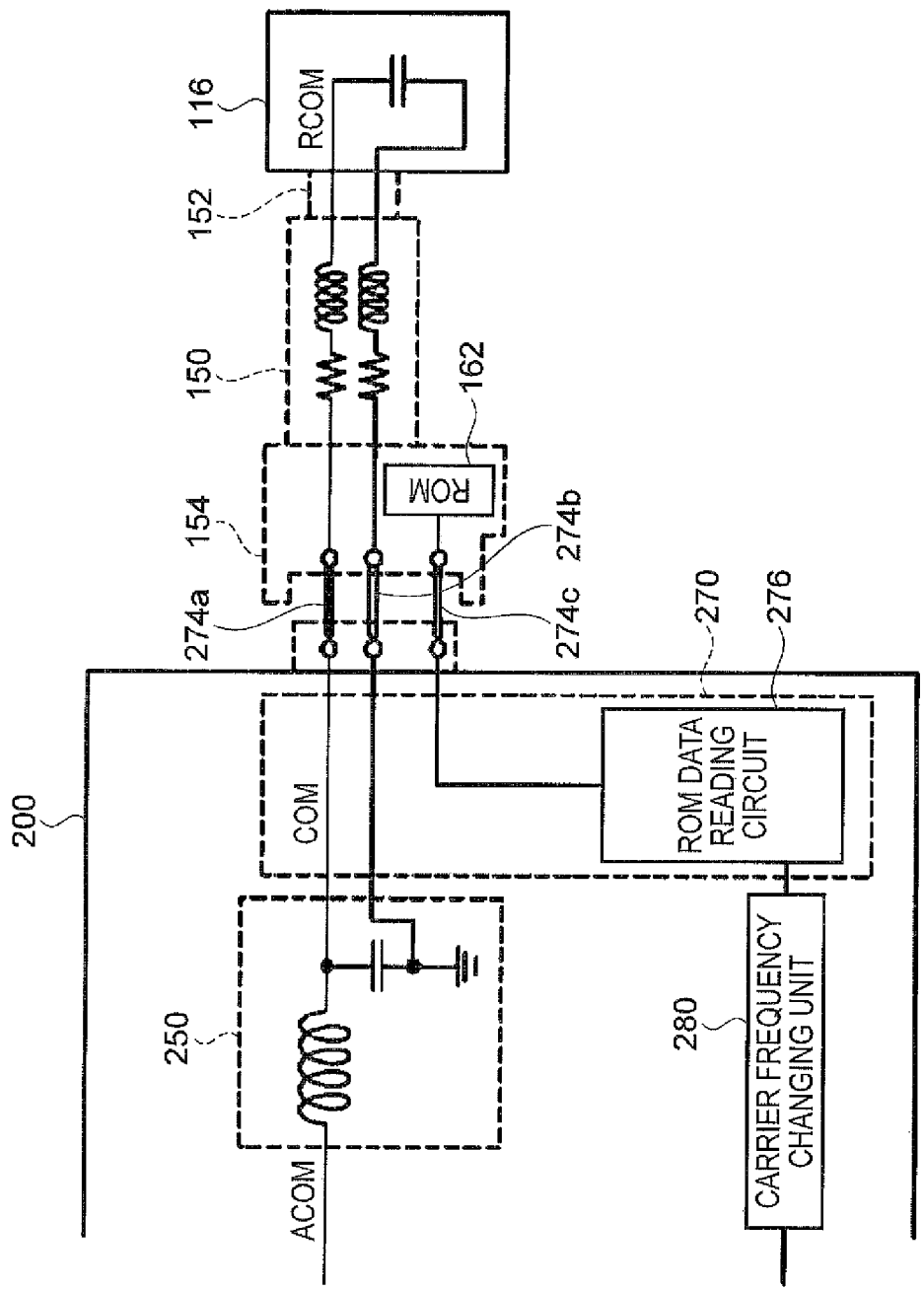
FIG. 10 is a circuit diagram illustrating a part of a capacitive load driving circuit according to a second example.

FIG. 10 is a circuit diagram illustrating a part of a capacitive load driving circuit 200 of the example. Specifically, the ROM storing the connection line information is provided in the connector 154 of the connection cable 150. In the example, the ROM 162 is provided in the connector 154 of the connection cable 150 on the capacitive load driving circuit 200 side, and the capacitive load driving circuit 200 is provided with a ROM data reading circuit 276 as the connection line information acquiring unit that reads data of the ROM 162.

When the connection cable 150 is connected to the capacitive load driving circuit 200 of the control unit 130 and the control unit 130 is operated, the connection line information stored in the ROM 162 is read by the ROM data reading circuit 276 provided in the capacitive load driving circuit 200 and is input to the carrier frequency changing unit 280. On the basis of the correspondence shown in FIG. 7 or FIG. 9B described above, the carrier frequency corresponding to the connection line information is selected, and the pulse modulation is performed at the carrier frequency. In such a manner, it is possible to perform the pulse modulation at the carrier frequency corresponding to the connection cable 150, and thus it is possible to avoid that the carrier ripple is superimposed on the driving signal applied to the actuator 116.

F. Capacitive Load Driving Circuit of Third Example

In the second example described above, the connector 154 of the connection cable 150 on the control unit 130 (the capacitive load driving circuit 200) side is provided in advance with the ROM (storage medium) storing the connection line information as the configuration example of the connection line information acquiring unit 270. The connection cable 150 may be provided with an ID tag 160 corresponding to the cable length (or the characteristics of the cable) of the connection cable 150. In the example, the switch 272 corresponds to the "connection line information acquiring unit".

Figure 11:
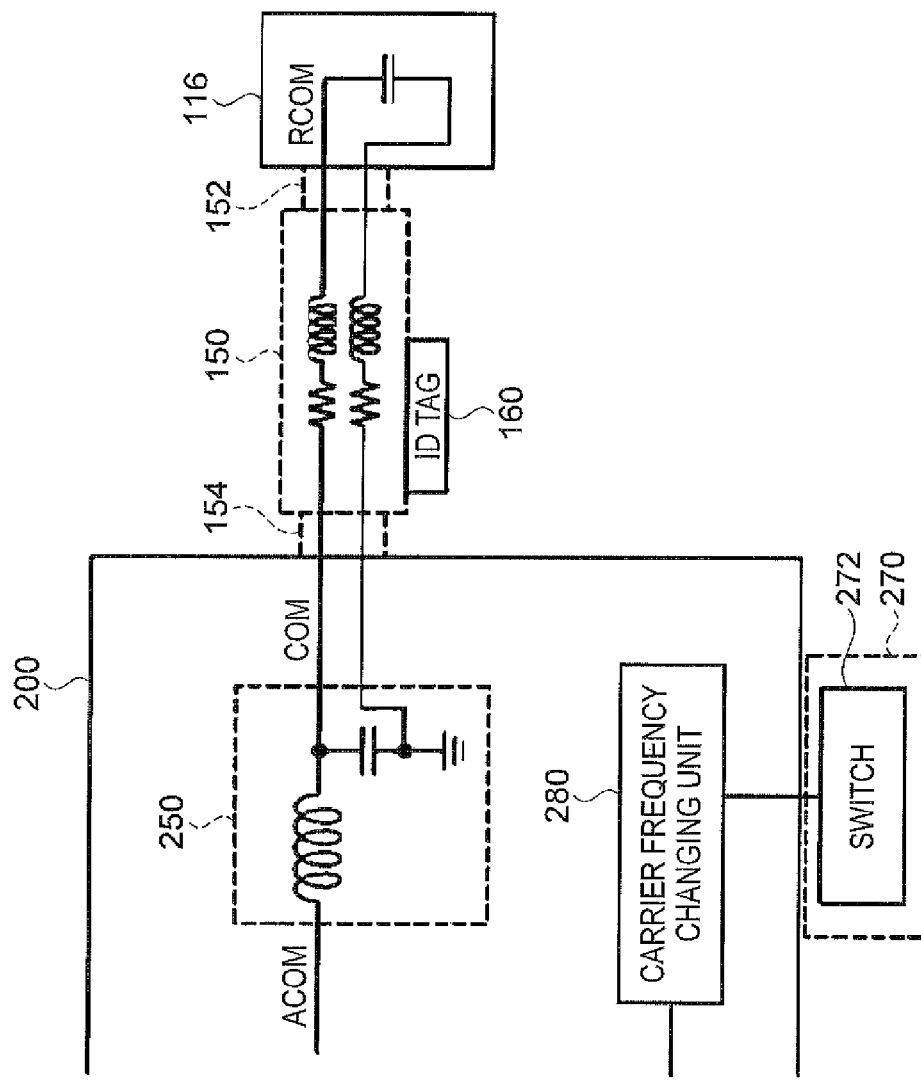
FIG. 11 is a circuit diagram illustrating a part of a capacitive load driving circuit according to a third example.

FIG. 11 is a circuit diagram illustrating a part of the capacitive load driving circuit 200 of the example. In the example, the connection cable 150 is provided with the ID tag 160 corresponding to the cable length (or the characteristics of the cable) of the connection cable 150. At the time of starting the control unit 130, an operator of the liquid ejecting device 100 reads the connection line information (the cable length or the characteristics of the cable) recorded in the ID tag 160, and the ON/OFF of the switch 272 is set, thereby inputting the connection line information to the carrier frequency changing unit 280. Then, the carrier frequency changing unit 280 changes the carrier frequency on the basis of the input connection line information. The modulation circuit 230 performs the pulse modulation on the WCOM using the changed carrier frequency. On the basis of the correspondence shown in FIG. 7 or FIG. 9B described above, the carrier frequency corresponding to the connection line information is selected, and the pulse modulation is performed at the carrier frequency. However, in the example, the connection line information is "0" when the switch 272 is turned off, and the connection line information is "1" when the switch 272 is turned on. In such a manner, it is possible to perform the pulse modulation at the carrier frequency corresponding to the connection line cable 150, and thus it is possible to avoid that the carrier ripple is superimposed on the driving signal applied to the actuator 116.

G. Liquid Ejection Type Printing Apparatus (Printer)

Figure 12A:
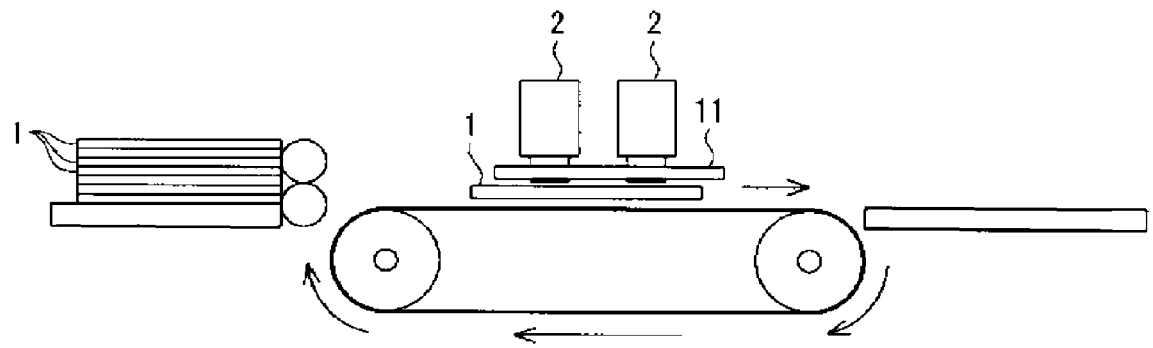
FIG. 12A and FIG. 12B are schematic diagrams illustrating an embodiment of a liquid ejection type printing apparatus using the capacitive load driving circuit.
Figure 12B:
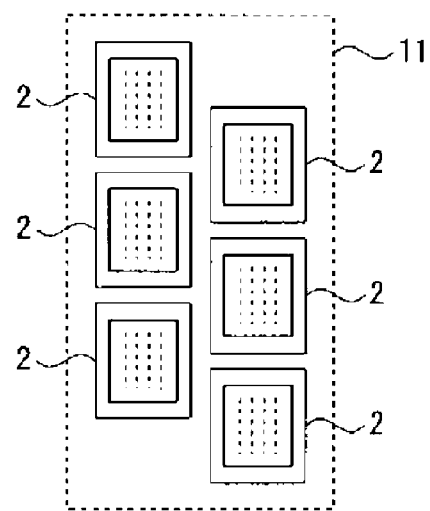

FIG. 12A and FIG. 12B are schematic diagrams illustrating an embodiment of a liquid ejection type printing apparatus using the capacitive load driving circuit of the example. FIG. 12A is a front view illustrating a schematic configuration. FIG. 12B is a plan view illustrating a vicinity of a liquid ejecting head.

The liquid ejection type printing apparatus of the example includes the capacitive load driving circuit (not shown) described in the example, a liquid tank (not shown) that supplies a liquid through a liquid supply tube, a liquid chamber (not shown) into which the liquid supplied from the liquid tank flows, an actuator (not shown) that is a capacitive load, and a plurality of liquid ejecting head (ejecting unit) 2 that has ejection nozzles for ejecting the liquid flowing into the liquid chamber. The liquid ejection type printing apparatus ejects the liquid flowing into the liquid chamber from the ejection nozzles by applying the driving signal to the actuator.

In the liquid ejection type printing apparatuses, an apparatus in which the liquid ejection head 2 mounted on a movement body called a carriage and provided with the liquid ejection nozzles is moved in a direction crossing a transport direction of a printing medium is generally called a "multi-pass type printing apparatus". An apparatus in which the liquid ejecting head that is longitudinal in the direction crossing the transport direction of the printing medium is disposed and it is possible to perform printing in so-called one pass is called a "line head type printing apparatus".

Reference numeral 2 in FIG. 12A denotes the plurality of liquid ejecting heads provided above the transport line of the printing medium 1. The liquid ejecting heads are in two rows in the transport direction of the printing medium, are arranged in the direction crossing the transport direction of the printing medium, and are fixed to a fixing plate 11. The plurality of nozzles are formed on the bottom faces of the liquid ejecting heads 2, and the face is called a nozzle face. As shown in FIG. 12B, the nozzles are disposed in a row in the direction crossing the transport direction of the printing medium for each color of the ejected liquid, the row is a nozzle row, and the row direction is a nozzle row direction. A line head over the whole length of the width in the direction crossing the transport direction of the printing medium 1 is formed by the nozzle rows of all the liquid ejecting heads 2 provided in the direction crossing the transport direction of the printing medium. When the printing medium 1 passes under the nozzle faces of the liquid ejecting heads 2, the liquid is ejected from the plurality of nozzles formed on the nozzle faces to perform printing.

In the liquid ejecting head 2, liquids such as inks with four colors of, for example, yellow (Y), magenta (M), cyan (C), and black (K) are supplied from the liquid tanks (not shown) of the colors through liquid supply tubes. Necessary amounts of liquids are simultaneously ejected from the nozzles formed on the liquid ejecting heads 2 to necessary parts, thereby outputting small dots on the printing medium 1. By performing this operation for each color, it is possible to perform the printing based on the so-called one pass only by allowing the printing medium 1 transported by a transport unit to pass once.

As a method of ejecting the liquid from the nozzles of the liquid ejecting head, an electrostatic method, a piezoelectric method, a film boiling method and the like are used. In the embodiment, the piezoelectric method is used. In the piezoelectric method, when a driving signal is applied to a piezoelectric element that is a nozzle actuator, a position of a vibration plate in a cavity is changed to change pressure in the cavity, thereby liquid droplets are ejected from the nozzles. It is possible to adjust the amount of ejected liquid droplets by adjusting a crest value of the driving signal or a voltage increase and decrease slope.

As shown in FIG. 12B, the line head type printing apparatus is provided with the plurality of liquid ejecting heads. In the example, each of the plurality of liquid ejecting heads is provided with the capacitive load driving circuit. The capacitive load driving circuit and the liquid ejecting head are connected by the connection cable 150 described above. However, since the plurality of liquid ejecting heads are disposed longitudinally in the direction crossing the transport direction of the printing medium, the connection cables 150 connecting the capacitive load driving circuit to the liquid ejecting head is provided with a proper length by the positional relationship between the liquid ejecting head and the capacitive load driving circuit.

Then, from the reason described above, a large carrier ripple may be superimposed on at least a part of the plurality of liquid ejecting heads, according to the length of the cable. As a result, in the liquid ejection type printing apparatus, it is difficult to control proper ejection of the liquid droplets, and image quality of a printed matter may be decreased.

Even in such a case, according to the example, it is possible to perform the pulse modulation at the carrier frequency corresponding to the connection cable 150, and thus it is possible to avoid that the carrier ripple is superimposed on the driving signal applied to the actuator 116. As a result, it is possible to avoid the decrease of the image quality of the printed matter. The example may be similarly applied to the liquid ejecting methods other than the piezoelectric method.

The capacitive load driving circuits of various examples have been described, but the invention is not limited to all the example, and may be variously embodied within the scope which does not deviate from the main concept thereof. For example, by applying the capacitive load driving circuit of the example to various electronic apparatuses including medical apparatuses such as a fluid ejecting device used to form a micro-capsule containing medicine or nutritional supplement, it is possible to provide a small-sized electronic apparatus with high power efficiency. The invention may be preferably applied to a capacitive load driving circuit that is mounted on an ink jet printer and drives ejection nozzles for ejecting ink.

This application claims priority to Japanese Patent Application No. 2011-176576, filed on Aug. 12, 2011, the entirety of which is hereby incorporated by reference.

What is claimed is:

1. A liquid ejecting device comprising:
an ejection unit that has a nozzle, a liquid chamber connected to the nozzle and having a variable volume, and a liquid communication pipe communicating the nozzle with the liquid chamber;
a capacitive load that extends by a driving signal application and changes a volume of the liquid chamber; and
a capacitive load driving circuit that drives the capacitive load by the driving signal application,
wherein a liquid flowing into the liquid chamber is ejected from the nozzle by changing the volume of the liquid chamber, and
wherein the capacitive load driving circuit includes
a driving waveform signal generating circuit that generates a driving waveform signal that is a driving signal reference,
a modulation circuit that performs pulse modulation on the driving waveform signal to generate a modulation signal,
a digital power amplifier that amplifies power of the modulation signal to generate a power amplification modulation signal in the form of a pulse wave,
a low pass filter that smoothes the power amplification modulation signal in the pulse wave to generate the driving signal,
a connection cable that connects the low pass filter to the capacitive load and is provided such that at least one of the low pass filter and the capacitive load is detachable,
a connection line information acquiring unit that acquires connection line information associated with the connection cable, and
a carrier frequency changing unit that changes a carrier frequency when the modulation circuit performs the pulse modulation on the driving waveform signal, on the basis of the connection line information.

2. The liquid ejecting device according to claim 1, wherein the connection line information is information associated with an inductance value or an impedance value of the connection cable.

3. The liquid ejecting device according to claim 1, wherein the connection cable has a first protruding terminal to which the driving signal is transferred from the low pass filter,
wherein the connection line information acquiring unit acquire the connection line information by detecting whether or not a second protruding terminal to which the driving signal is not transferred is provided with the connection table.

4. The liquid ejecting device according to claim 3, wherein the second protruding terminal is configured by an optical plug in which optical fibers are combined.

5. The liquid ejecting device according to claim 1, wherein the connection cable is provided with a storage medium readably storing the connection line information, and
wherein the connection line information acquiring unit is a unit that reads the connection line information from the storage medium.

6. A medical apparatus using the liquid ejecting device according to claim 1.

7. A printing apparatus using the liquid ejecting device according to claim 1.

* * * * *